United States Patent [19]
Flotte et al.

[11] Patent Number: 5,658,892
[45] Date of Patent: Aug. 19, 1997

[54] COMPOUND DELIVERY USING HIGH-PRESSURE IMPULSE TRANSIENTS

[75] Inventors: Thomas J. Flotte, Boston; Apostolos G. Doukas, Belmont; Daniel J. McAuliffe, Boxford, all of Mass.; Therese M. Anderson, Oakland, Calif.

[73] Assignee: The General Hospital Corporation, Boston, Mass.

[21] Appl. No.: 385,043

[22] Filed: Feb. 7, 1995

Related U.S. Application Data

[63] Continuation-in-part of Ser. No. 236,265, May 2, 1994, which is a continuation of Ser. No. 6,064, Jan. 15, 1993, abandoned.

[51] Int. Cl.$^6$ ................................................. A61K 31/70
[52] U.S. Cl. .................... 514/44; 536/22.1; 536/23.1; 204/155; 204/157.15; 607/72
[58] Field of Search .................... 514/44; 536/22.1, 536/23.1; 204/155, 157.15, 157.6; 607/72

[56] References Cited

U.S. PATENT DOCUMENTS

| | | | |
|---|---|---|---|
| 4,649,151 | 3/1987 | Dougherty et al. | 514/410 |
| 4,651,739 | 3/1987 | Oseroff et al. | 128/395 |
| 4,656,186 | 4/1987 | Bommer et al. | 514/410 |
| 4,658,023 | 4/1987 | Shudo | 540/145 |
| 4,675,338 | 6/1987 | Bommer et al. | 514/410 |
| 4,971,991 | 11/1990 | Umemura et al. | 514/410 |
| 5,380,411 | 1/1995 | Schlief | 204/157.15 |
| 5,403,590 | 4/1995 | Forse | 424/422 |

OTHER PUBLICATIONS

Kasuya et al. *Reza Kenkyu*, vol. 15(8): 624–635, (1987) Abstract only.

Karu et al. *Kvantovaya Elektron.*, vol. 8(12):2540–5, (1981) Abstract only.

Karu et al. *Kvantovaya Elektron.*, vol. 9(1): 141–4, (1982) Abstract only.

Karu et al. *Lett. Nuovo Cimento Soc. Intel. Fis*, vol. 32(2): 55–9, (1981) Abstract only.

Pastushenko et al. *Biol. Membr.*, vol. 9(2): 223–232, (1992).

Berens et al., "Effect of Acoustic Shock Waves on Clonogenic Growth and Drug Sensitivity of Human Tumor Cells in vitro," J. Urology 142:1090–1094, 1989.

Boh et al., "Extracorporeal Photopheresis," International Journal of Dermatology, 33:407–411, 1994.

Christensen et al., "Photopheresis in the 1990s," J. of Clinical Aphersis 6:216–220, 1991.

Gambihler et al., "Permeabilizatin of the Plasma Membrane of L1210 Mouse Leukemia Cells Using Lithotripter Shock Waves," J. Membrane Biol. 141:267–275, 1994.

Holmes et al., "Altered Neutrophil Permeability Following Shock Wave Exposure in vitro," The Journal of Urology, 147:733–737, 1992.

Holmes et al., "The Combined Effects of shock Waves and Cisplatin Therapy on Rat Prostate Tumors," J. Urology 144:159–163, 1990.

McCormack et al., "The Tumoricidal Potential of Extracorporeal Shock Wave Therapy," European Journal of Surgical Oncology 19:232–234, 1993.

(List continued on next page.)

*Primary Examiner*—John Kight
*Assistant Examiner*—Howard C. Lee
*Attorney, Agent, or Firm*—Fish & Richardson P.C.

[57] ABSTRACT

A method of increasing delivery of a compound from an exterior region to an interior region of a cell without causing substantial lethality to the cell. The method includes the steps of first providing the compound in the exterior region proximal to a membrane of the cell, and then exposing the membrane to a time-dependent impulse transient characterized by a rise time and a magnitude. In this manner, the exposing step temporarily increases the permeability of the membrane, resulting in an increase in the diffusion of the compound from the exterior region to the interior region thereby enhancing the delivery of the compound without causing substantial lethality to the cell.

31 Claims, 8 Drawing Sheets

OTHER PUBLICATIONS

Oosterhof et al., "Effects of High-Energy Shock Waves Combined with Biological Response Modifiers in Different Human Kidney Cancer Xenografts," Ultrasound in Medicine and Biology, 17:391–399, 1991.

Randazzo et al., "The in vitro and in vivo Effects of Extracorporeal Shock Waves on Malignant Cells," Urol. Res. 16:419–426, 1988.

de Reijke et al., "Tumor Growth Delay by Laser–Generated Shock Waves," Lasers in Surgery and Medicine 14:205–212, 1994.

Russo et al., "High Energy Shock Waves Suppress Tumor Growth in vitro and in vivo," J. Urol. 135:626–628, 1986.

Umemura et al., "Mechanism of Cell Damage by Ultrasound in Combination with Hematoporphyrin," Jpn. J. Cancer Res. 81:962–966, 1990.

Vivino et al., "Stable Cavitation at low Ultrasonic Intensities Induces Cell Death and Inhibits $^3$H–TdR Incorporation by Con–A–Stimulated Murine Lymphocytes in vitro," Ultrasound Med. Biol. 11:751–759, 1985.

Yumita et al., "Synergistic Effect of Ultrasound and Hematoporphyrin on Sarcoma 180," Jpn. J. Cancer Res. 81–304–308, 1990.

Yumita et al. "Hematoporphyrin as a Sensitizer of Cell–Damaging Effect of Ultrasound," Jpn. J. Cancer Res.80:219–222, 1989.

Zhong et al., "Differing Modes of Shock–Wave Generation," Seminars in Urology, XII:2–14, 1994

Kasuya et al., "Gene Transfection by Laser Cell Surgery." The Review of Laser Engineering. vol. 15, No. 8, pp. 41–52, Aug. 1987.

COMPOUND DELIVERY USING HIGH-PRESSURE IMPULSE TRANSIENTS

This application is a continuation-in-part application of U.S. Ser. No. 08/236,265 entitled "HIGH ENERGY IMPULSE CHEMOTHERAPY", filed May 2, 1994, which is a continuation of U.S. Ser. No. 08/006,064, filed Jan. 15, 1993, now abandoned.

STATEMENT AS TO FEDERALLY SPONSORED RESEARCH

Partial funding for the work described herein was provided by the U.S. Government, which has certain rights to the invention.

BACKGROUND

The invention relates to the use of high-pressure impulse transients to deliver compounds to cells.

Laser light incident on an absorbing material results in deposition of heat in the irradiated region, resulting in thermal expansion or contraction. Thermal expansion, in particular, may result in the launching of impulse transients which propagate through the material at high velocities. Depending on the nature of the irradiating optical field and the host material, impulse transients can be either acoustic waves, i.e., low-pressure waves propagating at sonic speeds, or shock waves, i.e., high-pressure waves propagating at supersonic speeds. The latter may be generated, for example, when the absorption of laser radiation is followed by a rapid phase change (e.g., evaporation or plasma formation) of the irradiated region.

Shock waves typically have fast rise times, resulting in a discontinuity in pressure, density, particle velocity (i.e., the displacement velocity behind the shock front), and internal energy. For instance, in water, the rise time of a shock wave having a pressure of about 100 kbar is on the order of a picosecond; this corresponds to a shock front having a thickness of about 2–5 nm (Harris and Presles, J. Chem. Phys. 77:5157–5164, 1982).

Shock waves generated in tissue may result in cellular damage. In particular, the effects of waves induced using extracorporeal lithotriptors has been extensively studied (see, e.g. Brummer et al., Ultrasound Med. Biol. 15:229–239, (1989). These experiments show that shock wave-induced cavitation generated following optical absorption may be responsible for the cell damage, and that such damage may cause retardation of rapidly proliferating tissue, such as tumors.

The combination of shock waves and drugs has also been used to kill cells. Holmes et al. (J. Urol. 144:159–163, 1990), for example, describe the treatment of prostate tumors in rats using high-pressure, short-duration waves in combination with cisplatinum. In these experiments, although delayed tumor growth was achieved, an increase in animal mortality (relative to cisplatinum alone) was observed when the applied compound was combined with shock wave therapy. For example, Berens et al. (J. Urol. 142:1090–1094, 1989) used spark-induced pressure waves, followed by therapy with several chemotherapeutic agents, to decrease tumor cell proliferation.

In a related application, following interaction with shock or pressure waves, pressure-sensitive drugs may become toxic, resulting in cell killing. Experiments of this sort are described, for example, in Umemura et al., Jap. J. Canc. Res., 81:962–966 (1990).

For many laboratory and therapeutic situations it is desirable to increase the concentration of compounds within a selective group of cells either ex vivo or in vivo. For example, chemotherapy for cancer is made more effective when the cytotoxic agent can be provided to the tumorous tissue in higher concentrations than in surrounding healthy tissues. Similarly, the success of many gene therapy methods is dependent upon the increased delivery of nucleic acids to certain cell types or body regions. Methods for delivering compounds to certain cell types or locations have been attempted using, for example, retroviral vectors, microinjection, calcium phosphate transfer, asialorosomucoid-polycysine conjergation, lipid-mediated delivery, and electroporation. There are many applications for which these systems are ineffective for increasing the concentration of a chosen compound within a given cell type or for which such a method is otherwise inappropriate.

SUMMARY

We have discovered methods for delivering a large variety of compounds to living cells. These methods have the advantage of being localized, useful in vivo and ex vivo, and causing very little cellular lethality.

In general, in one aspect, the invention features a method for increasing delivery of a compound from an exterior region to an interior region of a cell in a manner which does not cause substantial cellular lethality when a non-cytotoxic compound is employed. The method includes the steps of first providing the compound in the exterior region proximal to a membrane of the cell, and then exposing the membrane to a time-dependent impulse transient characterized by a rise time and a magnitude. The exposing step temporarily increases the permeability of the membrane, resulting in an increase in the diffusion of the compound from the exterior region to the interior region, thereby enhancing the delivery of the compound to the cell. Preferably, interaction of a group of cells with the impulse transients results in at least 5% of the cells surviving; more preferably, at least 50% of the cells survive, and most preferably at least 90% of the cells survive. These methods may be applied in virtually any situation where other methods for mediating the entry of compounds into cells are currently in use.

In preferred embodiments, the exposing further includes generating the impulse transient in the exterior region of the cell, and then allowing the transient to propagate until incident on the cell membrane. The generating step preferably includes impulsively exciting the exterior region of the cell using a rapid, time-dependent force. In one embodiment, the time-dependent force results from thermoelastic expansion of the exterior region. Preferably, in this case, the generating step includes depositing over a short time period an amount of heat in the exterior region; here, the heat results in thermal expansion to cause the time-dependent force. Most preferably, the heat is generated using a pulsed optical source (e.g., a laser) emitting a wavelength which is absorbed by a portion of the exterior region.

Alternatively, in another embodiment, the rapid, time-dependent force is generated using a transducer. Preferably, the transducer is in direct contact with the exterior region, and undergoes rapid displacement following application of an optical, thermal, or electric field to generate the impulse transient. The transducer is preferably ablated using the applied optical field to cause the rapid displacement. In another embodiment, the transducer undergoes piezoelectric expansion following application of the electrical field to cause the rapid displacement. In still other embodiments, the transducer undergoes thermal expansion following application of heat or a plasma to cause the rapid displacement.

In preferred embodiments, the rise time of the impulse transient is characterized by a time constant of between 1 and 150 nanoseconds; most preferably, the time constant is below 35 nanoseconds. The magnitude of the transient is preferably characterized by a pressure of between 1 and 500 barrs, and most preferably a pressure of between 250 and 350 barrs. Multiple impulse transients having these properties may be used during the exposing step.

In other embodiments, the providing step includes directly applying the compound to the exterior region proximal to the cell. For instance, the compound may be applied to a solution in the exterior region, and the cell is then exposed to the impulse transient in vitro. In another embodiment, the providing step includes administering the compound to a patient prior to the exposing step (e.g., by general or localized injection or by any other means of pharmaceutical administration appropriate for the chosen compound), and then exposing the cell to the impulse transient in vivo. Here, the patient is preferably a human patient. Preferably, the exposing step is extracorporeal, or is done during invasive surgery.

Where the patient is a human patient, the method may be used in any situation where enhanced local delivery of a compound is desirable. Gene therapy applications such as the delivery of the Factor IIX encoding gene to stem cells or the delivery of the TPA genes to vascular endothelia are only one class of possible applications. The methods may also be used to deliver therapeutic polypeptides, or other compounds of diverse molecular weights. In some cases, it will be desirable to provide multiple compounds.

The cell may be a diseased cell included in a region of diseased tissue. In this case, the compound preferably has a delivery index of at least 50, meaning that once delivered, the amount compound localized in a region of healthy tissue is less than 50 percent of the level of the compound present in the diseased tissue.

In other preferred embodiments, the compound delivered to the cell includes a nucleic acids, and may be, for example, a gene with or without flanking DNA sequences.

By "rapid, time-dependent force" is meant that the force has a short time duration relative to the time required for the impulse transient to propagate away from the region of excitation. Similarly, by a "short time period" is meant a time period which is short relative to the time required for propagation of the impulse away from the excited region.

By "exterior region" is meant a region outside of the cell membrane. Such regions may include other cells, cell-supporting matrices, gels, buffer solutions, water, saline, agar, or any other interfacial solutions. Thus, transducers in "direct contact with the exterior regions" include transducers in contact with solutions outside of the cell membrane as well as transducers in contact with cells other than the target cells.

By "enhancing the delivery" is meant that use of the impulse transient preferably allows between 0.01% and 1% of the exposed cells to receive the compound; more preferably, between 1% and 5% of the exposed cells receive the compound; most preferably, greater than 5% of the exposed cells receive the compound.

The invention has many advantages. In particular, during use with a compound or compounds, careful control over the rise time and magnitude of the impulse transient induces a time-dependent permeability in the exposed cell membrane while minimizing cavitation effects in the cell. This increases the diffusion of the compound into the cell for a short period of time, and allows, for example, effective delivery the compounds without causing destruction or cell killing. Thus, the method can be used for drug delivery or increasing the intercellular drug concentration. In this manner, a host of maladies may be treated by effectively delivering pharmaceutical compositions with the assistance of impulse transients; drugs which have been previously dismissed because they could not diffuse through cell membranes may be delivered using the method of the invention.

Because the applied transients do not cause permanent destruction, the method is additionally effective when used to transfect DNA into cells, and can therefore be used in gene therapy applications. In addition, because the method enhances the delivery of compounds to cells, lower levels of the therapeutic compound may be administered systemically to the patient. In particular, multiple high-pressure impulses have the surprising effect of dramatically increasing drug delivery to the cells, and thus allow lower levels of therapeutic compound to be administered to the patient. Thus, the method may be used to provide localized administration of compounds which are otherwise too toxic to surrounding tissue to have therapeutic utility.

In addition, the impulse transients are most preferably induced with optical sources, and can therefore be used to non-destructively deliver compounds to select regions of tissue with high spatial resolution. Thus, during in vivo applications, small, local regions of cells can be effectively treated using oral or topical application of the compound, followed by irradiation using an easily controlled light source. Fiber optic delivery systems are particularly maneuverable, and may be used to irradiate tissue, thereby generating impulse transients in hard-to-reach places. These types of delivery systems, when optically coupled to lasers, are preferred as they can be integrated into catheters and related flexible devices, and used to irradiate most organs in the human body. In addition, in order to launch an impulse transient having the desirable rise times and magnitude, the wavelength of the optical source can be easily tailored to generate the appropriate absorption in a particular cell type; this allows a host of different cells to be effectively treated.

Other advantages will be apparent from the following detailed description, and from the claims.

DETAILED DESCRIPTION

Figure 1A:
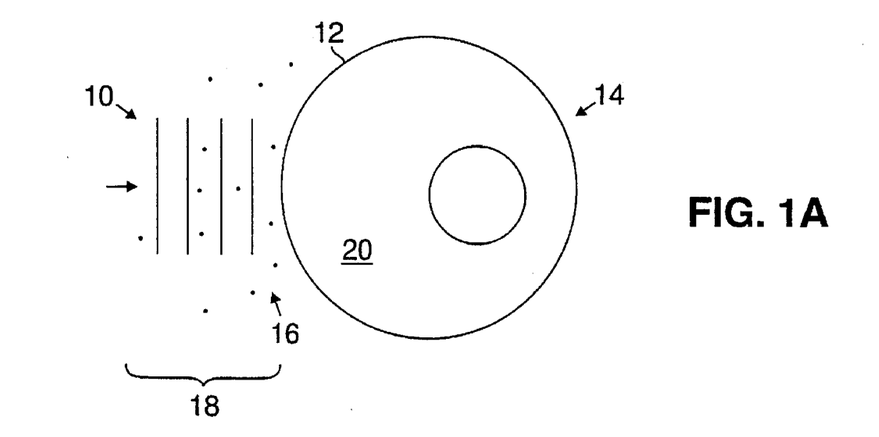
FIGS. 1A–1C are, respectively, schematic drawings of the impulse transient and an applied compound prior to, during, and following interaction with the cell.
Figure 1B:
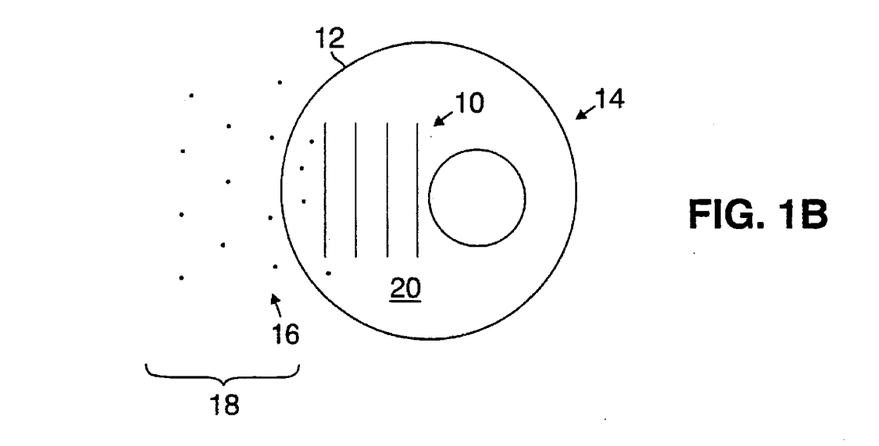
Figure 1C:
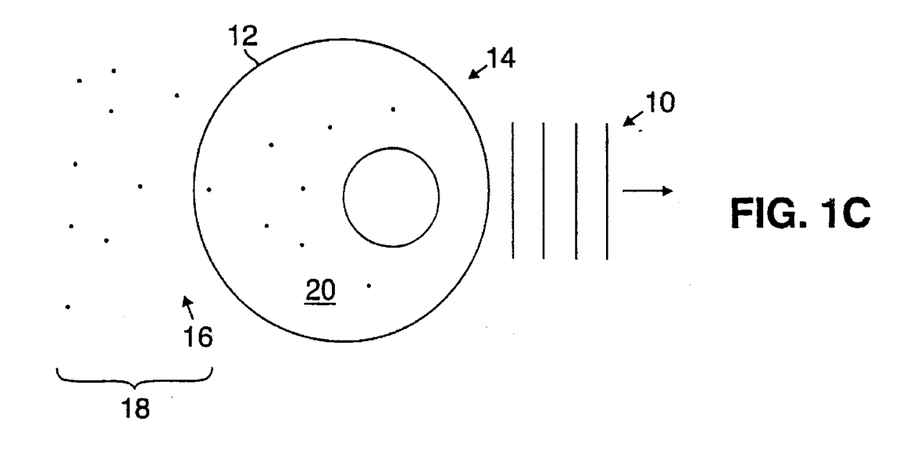

Referring first to FIGS. 1A–1C, impulse transients (indicated by the lines 10) having the time and intensity-dependent properties according to the invention induce a time-dependent permeability in a membrane 12 of a cell 14, thereby increasing diffusion of a compound 16 from an exterior region 18, across the membrane 12, and into the cell 14.

As shown in FIG. 1A, prior to exposure, the cell membrane (typically composed of lipid and phospholipid-type compounds, as well as cholesterol, glycolipids, and membrane proteins) may be impermeable to, foreign compounds; this prevents diffusion of the compound into the cell. Exposure to the impulse transient, as shown in FIG. 1B, induces small perforations in a portion of the membrane, thus allowing the compound to diffuse across the membrane and become internalized by the cell. Diffusion, in general, is dictated by the sizes of the perforation induced in the membrane and the compound to be delivered, and by the pressure difference between the external region 18 and the cell interior 20. Increases in the size of the hole relative to the compound and in the pressure of the external region 18 relative to the cell interior 20 will increase the rate of diffusion. Typically, using impulse transients having the temporal and intensity-dependent properties described herein, compounds having a size of a few hundred kDs may diffuse into the incurred holes. More preferably, the holes are large enough to pass 1000-kD compounds; most preferably, the holes are large enough to pass compounds as large as 7000 kDs. In addition, electrostatic forces existing between the cell membrane and the compound may also effect the rate of diffusion. For example, the phospholipids of the membrane are typically positively charged, and will thus partially repel compounds with high positive charges. Diffusion may also be pH dependent.

The amount of compound 16 delivered to the cell 14 will also depend on the time period during which the membrane 12 is permeable, and the size of the portion of the membrane which is made permeable. Typically, this portion represents about 3–4% of the membrane; as is discussed in detail below, the extent of permeability is dependent on the rise time, waveform shape, and intensity of the impulse transient.

The cell is made permeable for a finite time period. Based on optical imaging studies using dyes as the delivered compounds, it is estimated that this time period is on the order of between about 1 and 10 seconds. Once this period has elapsed, the cell is no longer permeable, and the compound is unable to diffuse into (or out of) the cell.

As is indicated by FIG. 1C, the impulse transients preferably have durations on the order of a few tens of nanoseconds, and thus interact with the cell for only a short period of time. Following this time period, the impulse transient passes through the cell and into the surrounding tissue, where it may expose other cells or be attenuated and dispersed into the surrounding medium. Following interaction with the impulse transient, the cell is not permanently damaged in any way, and proceeds to process the internalized compound.

The impulse transient may be generated by any known means, including optical sources (e.g., lasers), lithotriptors, piezoelectric devices, high-velocity projectiles, and localized explosive devices. In the case of laser-induced impulse transients, the physical phenomenon responsible for launching the transient is, in general, chosen from a group consisting of three mechanisms: 1) thermoelastic generation; 2) optical or dielectric breakdown; or 3) light or heat-induced ablation or plasma formation. Most preferably, a laser is used to induce the impulse transient, and the mechanism responsible for the wave generation is laser-induced ablation. Dielectric breakdown may also be used, and is typically induced by a high-voltage spark or piezoelectric transducer (one example is the extracorporeal lithotriptor; Coleman et al. Ultrasound Med. Biol. 15:213–227 (1989)). Ablation may be initiated directly in the external region, or on a polymeric or metallic foil coupled to the tissue via a gel or oil (Zweig and Deutsch Appl. Phys. B54:76–82 (1992); Yang, J. Appl. Phys. 45:2601–2608 (1974); Wantanabe et al., J. Invest. Dermatol. 90:761–766, 1988)).

Figure 2A:
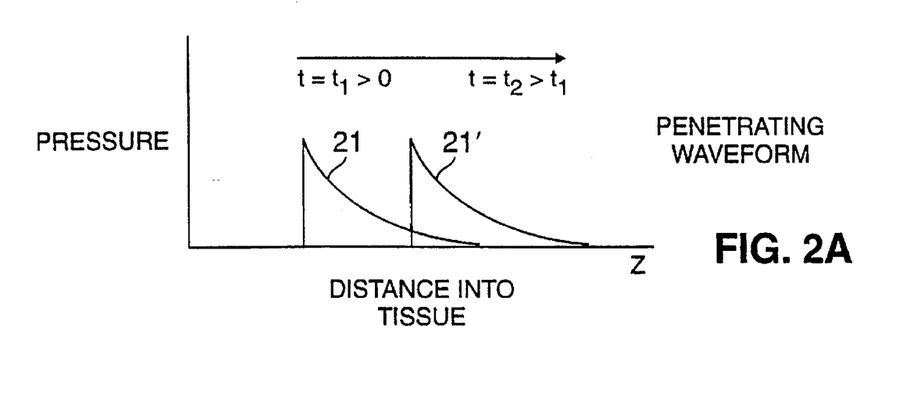
FIGS. 2A–2C are schematic plots showing the time evolution of, respectively, the penetrating, reflected, and collective impulse transients.
Figure 2B:
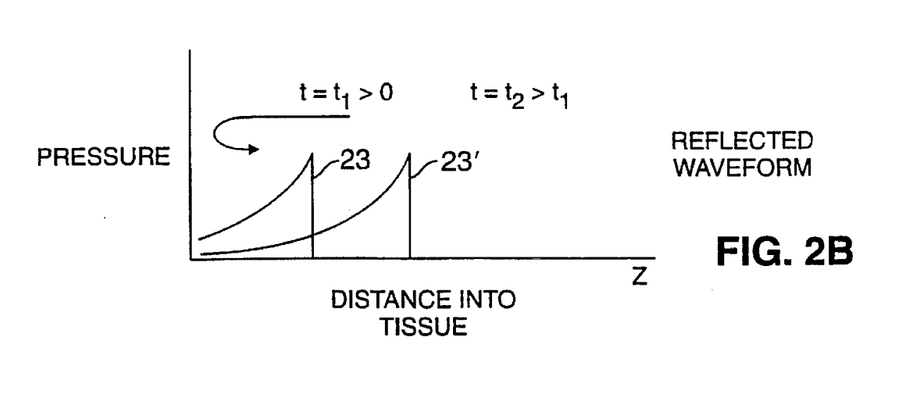
Figure 2C:
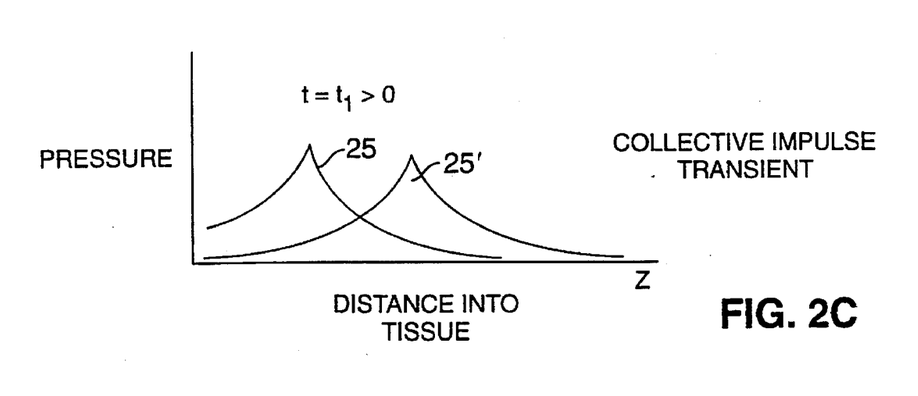

Referring now to FIGS. 2A–2C, during thermoelastic generation of impulse transients, absorption of optical radiation by the host tissue results in heating of the tissue along a surface, followed by the launching of a pair of impulse transient waveforms 21, 23. At time $t_1$, the first waveform 21 propagates at the speed of sound and penetrates deeper into the tissue; the second waveform 23 propagates toward the surface, where it is at least partially reflected. The acoustic properties (i.e., density and impedance matching) at the tissue/external medium interface determine whether or not the second waveform 23 will be reflected by the surface. In general, large impedance differences between the tissue and the external medium result in complete reflection of the second waveform. Combination of the two impulse transient waveforms 21, 23 results in a collective impulse transient 25 which has both finite rise and decay times. At the later time $t_2$, the collective impulse transient 25' is composed of the time-evolved penetrating 21' and reflected 23' waveforms.

The rise time and decay of the impulse transients are dependent on the absorption depth of an excitation light pulse in the tissue. The incident optical radiation may be centered in the ultraviolet, visible, or infrared spectral regions, and the wavelength may be varied to adjust the absorption depth. Wavelengths which are weakly absorbed will penetrate deeper into the tissue compared to wavelengths which are strongly absorbed. Most preferably, the wavelength is centered at about 2.9 microns for tissue samples, and about 193 nm for polyamide transducers. Because of their broad absorbance properties, nearly any wavelength can be used for metal transducers, although here it is preferable to use a wavelength which is minimally reflected by the metal.

In preferred embodiments, the invention provides for the delivery of relatively few discrete pulses of high positive amplitude to the patient, rather than a larger number of low-amplitude pulses which generally cause damage to the surrounding tissue. The number of impulse transients administered to the patient is typically less than 3000, more preferably less than 100, and most preferably less than 50. Preferably, if multiple optical pulses are used to generate the impulse transient, the time duration between sequential pulses is preferably long enough to prevent permanent damage to the cell; most preferably, this duration is between 1 and 20 seconds.

In a related embodiment, the optical pulse can be used to irradiate a strongly absorbing material (e.g., a metal or polymer film) placed in direct contact with the tissue, or coupled to the tissue using a gel or oil. In this case, the film acts as an optically triggered transducer; following absorption of light, the film undergoes rapid thermal expansion, or is ablated, to launch a impulse transient into the tissue. By choosing materials which have large thermal expansion coefficients (e.g., polyamide films), this method can be used to launch high-amplitude impulse transients; typically, metal and polymer films have high absorption coefficients in the visible and ultraviolet spectral regions. In the case where the impulse transient is induced using other means, such as a piezoelectric transducer, the duration of the impulse transient is determined directly by the time-dependent action (i.e., expansion and contraction) of the transducer.

As described above, impulse transients are effectively generated by heat deposited in a small region of tissue during a short period of time (i.e., impulsive excitation). In general, in order to launch the impulse transient, the tissue must be heated over a time duration which is short relative to the time required for optical penetration into the medium. In addition, the heating time must be short relative to the time scales of acoustic propagation and thermal relaxation in the tissue (i.e., $\tau_u < \alpha(\lambda)^{-1} c_s^{-1}$, where $\tau_u$ is the pulse width of the impulse transient, $\alpha(\lambda)$ is the absorption coefficient of the sample at the wavelength $\lambda$ of the absorbed light, and $c_s$ is the speed of sound in the tissue). Under these conditions, the temperature change as a function of depth, $\Delta T(z)$, is given by $$\Delta T(z) = \Delta T_0 \exp[-\alpha(\lambda)z] \quad (1)$$

where the surface is at z=0 and $\Delta T_0$ is the temperature rise at the surface. In this case, the stress wave at the surface is reflected as a compression wave.

If the optical field used to generate the impulse transients contains a series of pulses at a repetition rate higher than the acoustic response of the material, a series of impulse transients may be generated to form a resulting waveform. In this case, the collective time-dependent characteristics of the resulting waveform are determined by the characteristics of the exciting pulse train. For example, the envelope of the exciting pulse train and the envelope of the resulting waveform may be similar.

Pulsed radiation can be generated by standard optical modulation techniques known in the art, such as by employing Q-switched or mode-locked lasers (using, for example, electro or acousto-optic devices). Lasers which can operate in a pulsed mode in the infrared, visible, and infrared spectrum include Nd:YAG, Nd:YLF, $CO_2$, excimer, dye, Ti:sapphire, diode, holmium (and other rare-earth materials), and metal-vapor lasers. The pulse widths of these light sources are adjustable, and can vary from several tens of picoseconds to several hundred microseconds. Most preferably, the optical pulse width is between about 100 picoseconds and 10 nanoseconds.

Figure 3A:
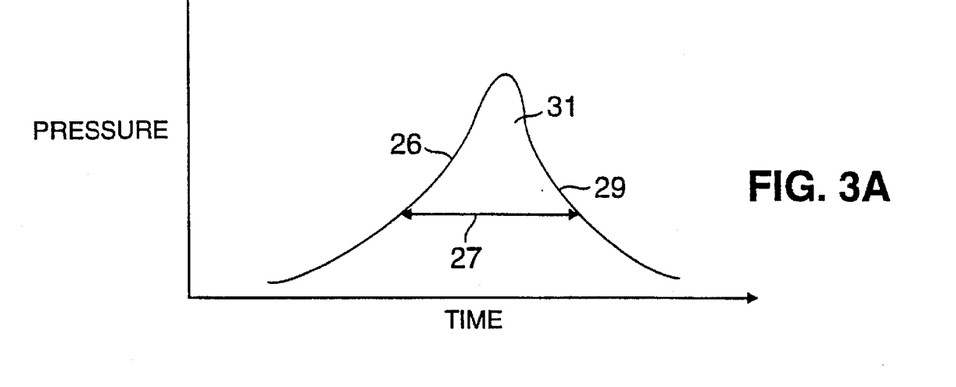
FIGS. 3A–3C are pressure-vs.-time plots of, respectively, the preferred impulse transients used according to the invention, the preferred impulse transient compared to transients having rise times which are too fast and too slow, and two successive impulse transients separated by a select time duration.
Figure 3B:
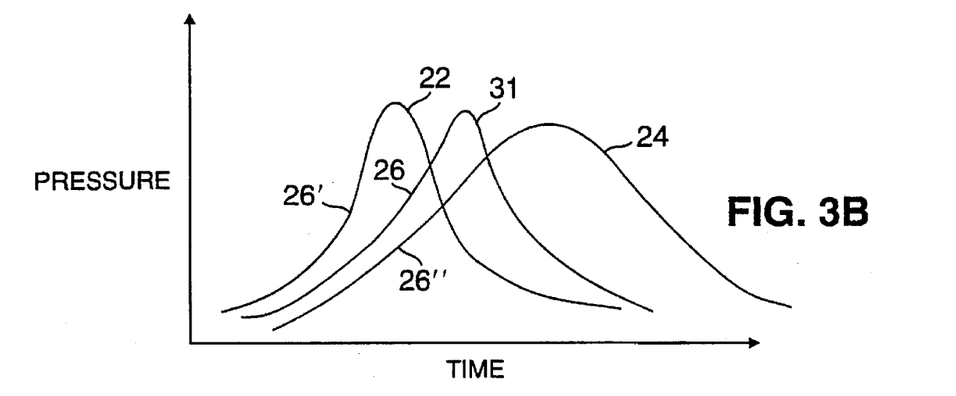
Figure 3C:
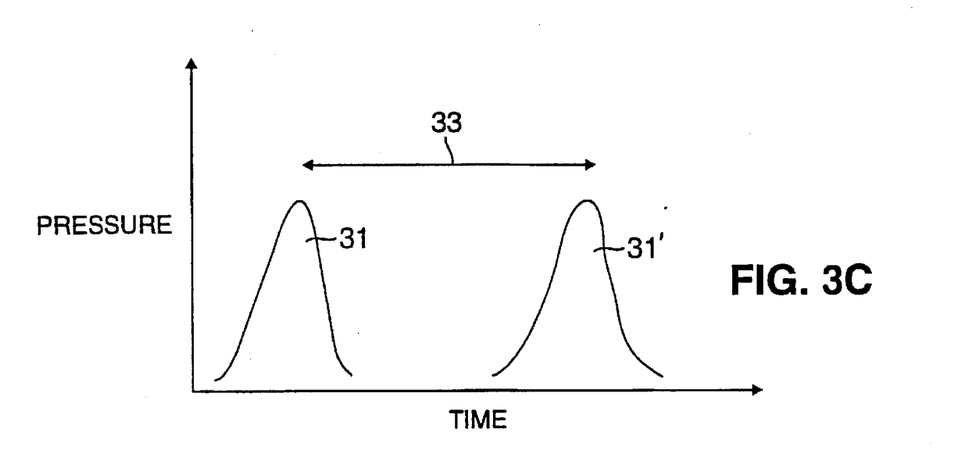

Referring to FIGS. 3A and 3B, the rise time 26, waveform shape, width 27, decay time 29 and magnitude of the impulse transient 31 are chosen to allow non-destructive temporary permeability of the cell membrane. In particular, the rise time of the impulse transient can significantly affect the cellular uptake of compounds. Preferably, the 10%-to-90% rise time 26 is less than 100 nanoseconds, and is most preferably between 1 and 25 nanoseconds. Waveforms 22 having rise times 26' which are too fast may result in permanent destruction in the cell, while waveforms 24 having rise times 26" which are too slow may result in little or no induced permeability to the cell, thereby limiting the amount of delivered compound. Referring now to FIG. 3C, when multiple impulse transients are used to enhance compound delivery to the cell, the time period used to separate successive impulse transients (indicated in the figure by the arrow 33) is determined, for example, by the time period separating incident optical pulses, and is preferably chosen to minimize permanent damage to the cell. The duration 33 can thus be adjusted by changing the repetition rate of the laser. For most light sources, this duration can be adjusted between several seconds and several hundred microseconds.

The magnitude of the impulse transient directly affects the degree of permeability induced in the cell, and is preferably between a pressure of about 100 and 500 barrs; most preferably, the pressure is between 250 and 350 barrs. Thus, in order to facilitate delivery of the compound to the cell, the impulse transient preferably delivers less than 50 barrs/ nanosecond, and most preferably less than 30 barrs/ nanosecond, to the cell membrane.

Impulse transients may be used to facilitate compound delivery to cells in vivo or in vitro. In the in vitro application, the transient may be used to deliver compounds to cells in culture, e.g., embryos in tissue culture or bone marrow. In in vivo applications, the compound is administered to the patient prior to generation of impulse transients in the region of interest. Compounds may be administered by local or systemic methods known in the pharmaceutical arts. For example, oral, topical, intravenous injection or intramuscular injections may be employed. After a time period to allow localization or dispersion of the compound, as appropriate, impulse transients are used to permeabilize the cells as described above, resulting in enhanced delivery of the compound or compounds to the cells of interest.

During in vitro applications, the method may be used to transfect cells with DNA, RNA, or other compounds of interest. In this case, prior to exposing the cells to impulse transients, the compound is provided in the media present in the external regions surrounding the cells. The appropriate dosage may be determined empirically using standard techniques known in the art. Once the compound is introduced to the cell-containing medium, exposure to impulse transients is carried out as described herein.

During in vivo applications, impulse transients are generated in patients using the guidelines for laser-based or ultrasonic therapies known in the art.

In a particular in vivo application, impulse transients may be generated using fiber optic delivery systems. For example, catheter technology in combination with a fiber optic pulse delivery system may be used for drug therapy and gene therapy in the cardiovascular system. Other related applications include gene therapy to affected organs such as the liver, heart, kidneys, pancreas, or brain, or to other cell types such as the skin, muscle or eye tissues.

In most in vivo applications, it is desirable to irradiate multiple layers of cells, and thus the preferred intensities and rise times of the impulse transients described herein allow the degree of induced permeability in the various cell layers to be maximized, while the permanent damage induced in these layers is minimized. Most tissues are composed primarily of water and have similar densities, and thus the propagation characteristics of impulse transients are relatively independent of the tissue type; in most cases, the impulse transients can propagate approximately a few centimeters into the exposed tissues without undergoing significant attenuation or spatial dispersion.

In addition, the characteristics of impulse transients generated in vivo may be altered during propagation. For example, during propagation in water-containing tissue, the rise time and waveform shape of the impulse transients are affected by the linear and nonlinear acoustic properties of the tissue medium. These properties may cause the peak of the impulse transient to propagate faster than the rest of the wave, resulting in a "self-steepening" of the leading edge. This may be desirable, as the degree of cellular permeability (and corresponding rate of drug delivery) is inversely related to the duration of the impulse transient rise time. The distance required to achieve self steepening depends upon the characteristics of the material (e.g., the density and mechanical properties), and the amplitude and rise time of the initial impulse transient.

In a particular example of self steepening, an optically generated impulse transient passing through 1 mm of vitreous typically experiences a decrease in rise time during the course of propagation. After travelling 1 mm, an original rise time of about 25 nanoseconds decreases to about 15 nanoseconds, indicating a self-steepening of the pulse in the nonlinear medium. Propagation of an impulse transient through the body of a patient is likely to experience a similar self-steepening effect, resulting in a modified waveform which is desirable for inducing permeability in a cell.

Figure 4:
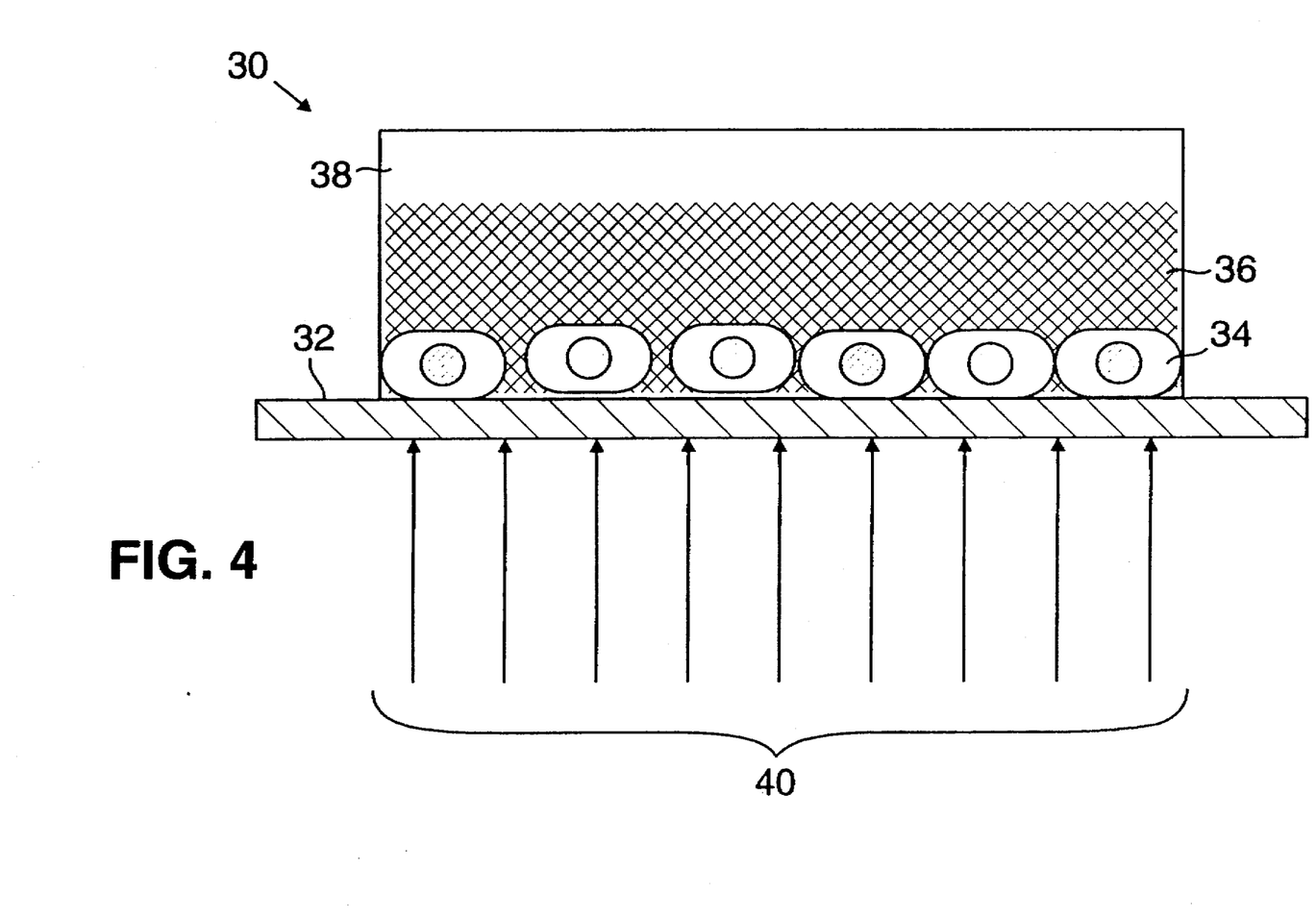
FIG. 4 is a somewhat schematic side view of a cell-supporting apparatus used to treat cells in vitro according to a method of the invention.

During in vitro delivery, an external, cell-supporting apparatus may be used to maximize the effects of impulse transients delivered to cells. Referring to FIG. 4, in one embodiment, an in vitro cell-supporting apparatus 30 features an absorbing film 32, such as a polyamide film, upon which a series of cells 34 are grown. The cells may be surrounded by a supporting substrate 36, such as a collagen gel, which preferably includes the compound to be delivered. In order to support the gel, the apparatus may further include a backing layer 38. During the exposure process, the absorbing film 32 is exposed to an optical field (indicated schematically by the arrows 40) which preferably ablates the film, thereby launching a impulse transient in the direction of the cells to increase the efficiency of the compound delivery.

In both in vivo and in vitro applications, different cell types typically exhibit similar mechanical properties, and are therefore expected to respond in a similar fashion to applied impulse transients. Similarly, cells from different types of animals should respond in the same general manner to the impulse transients.

Compounds which have a toxic effect at higher dosages may be administered to a patient using guidelines for administration which will produce greater concentrations of the drugs in the target tissues relative to the surrounding tissue, while maintaining adequate levels of the drug in the target. In general, this differential drug localization can be achieved using guidelines for administration determined using standard techniques known in the field of pharmacology. Preferably, the compound dosage and time course are such that a 2:1 or greater concentration ratio in the effected tissues relative to the surrounding tissues is achieved. Determining the appropriate dosage for a patient is a routine matter to one skilled in the art of pharmaceutical administration. Two approaches are commonly used to assay directly the quantity of drug in the diseased and surrounding tissues. First, tissue samples are obtained from animals/patients who have received different dosage and timing protocols. The quantity of drug in each tissue is then measured either chemically, or if there is a unique optical signal such as fluorescence, then by quantitative microscopy or laser-induced fluorescence. Impulses effective in yielding the desirable result may be obtained using any one of the impulse generating devices indicated above and calibrated so as to yield an impulse within the parameters described above. One skilled in the art may readily determine the optimal impulse parameters from within the provided scale for a given cell type, body region, and compound.

Systemically administered compounds which are useful in the invention are those which are taken up in greater amounts and/or retained substantially longer in the proliferating tissues relative to the surrounding tissues of a patient. Compounds with this characteristic can be defined as those which have a useful delivery index (defined above).

The drug is preferably chosen for delivery so that it is rapidly cleared from the rest of the body prior to delivery of the impulse transient. Localization of the compound is advantageous, as it allows impulse transients to be administered with highly localized effect to the area of the diseased cells, sparing healthy tissues of the body. In this way, the healthy vital organs are spared from the combination of the compound administered at sub-toxic doses, and the use of an impulse which by itself has no unacceptable effect on tissue viability.

Because the drugs administered may have little effect at the provided dosage in the absence of a high-pressure impulse transient, there should be little accompanying generalized toxicity in the patient outside the tissue of interest. The therapy can be administered either extracorporeally or during invasive surgery. Techniques for both methods of delivery are known to one skilled in the art.

As described above, the impulse transient works in combination with the therapeutic compound by generally increasing passive cell permeability in the region of administration.

The following examples are used to describe the enhancement of compound delivery using impulse transients.

EXAMPLE 1

Identifying Useful Compounds for Impulse Transient Therapy

The general method for identifying useful compounds and other parameters for impulse transient therapy is described below. In general, any cell type may be used to determine for the toxicity of a given compound prior to and in combination with the administration of high-pressure impulse transients. The general protocol is as follows:

Cell Culture

Immortalized cell lines are kept in tissue culture in the usual manner. Typically, EMT-6 mouse mammary carcinoma cells are utilized, but virtually any cell in culture may be utilized. The cells are resuspended in R.P.M.I. 1640 (GIBCO) with 10% fetal bovine serum (FBS) (GIBCO). The cultures are incubated at 37° C. in an atmosphere of 5% $CO_2$. Cultures of $2\times10^6$ cells per ml were established in flat-bottom culture plates (Fisher Scientific).

Gel

Denatured collagen (Knox gelatin) is added to phosphate buffered saline at 37° C. to make a 5% solution. Capillary tubes with 3 mil polyamide (Dupont, Wilmington, Del.) glued to one end are warmed to 37° C. 100,000 cells in 100 µl of the denatured collagen solution are added to each capillary tube at 37° C. The tubes are centrifuged at 1,200 RPM to bring the cells to the bottom, and are then placed in an ice bucket.

Impulse Generation

The polyamide is irradiated with a light source (e.g., an argon-fluoride excimer laser operating at 193 nm with a pulse of 14 nanoseconds, a fluence of 400 mJ/cm$^2$, and a repetition rate of 1 hertz).

Thymidine Incorporation

Following exposure to the impulse transients, cell-filled capillary tubes are put into the 37° C. water bath for 2 minutes. The polyamide is then removed from each capillary tube, and the contents are flushed with 0.5-ml complete medium into separate 5-ml test tubes containing 0.5 ml of complete medium. These test tubes are spun at 3200 r.p.m. for 10 minutes. After centrifugation, the supernatant in each tube is aspirated and discarded. Cell pellets are then resuspended with 200 µl of complete medium with 0.25 µCi of $^3$[H]-thymidine (sp. ac. 6.7 CI/mM; New England Nuclear, Boston, Mass.) and plated in a 96-well, flat-bottom microtiter plate. The plate is incubated for 4 hours. The cells are then disrupted, and the contents are collected on glass fiber filter strips and washed freely using an automated harvester (MASH II, Microbiological Associates, Walkersville, Md.). The dried filter papers are suspended in scintillation fluid and the radioactivity measured in a Beckman LS 3801 liquid scintillation spectrometer. The mean of the radioactive counts per minute (cpm) of the sample for each condition is calculated, and the means for cultures subjected to high-pressure impulses are expressed as a percentage of the control cultures.

Determination of Cell Survival and Compound Incorporation

Candidate compounds are tested for their utility by plating 100,000 cells/well in a 96-well plate and adding different quantities of the compound to different wells. All concentrations are replicated in 5 wells for accuracy. The quantities to be tested are generally known to one skilled in the art; however, a typical experiment may test the following concentrations (in µg/ml): 0.0, 0.001, 0.01, 0.1, 1.0, 2.0, 4.0, and 10.0. The cells are then incubated overnight and then the thymidine incorporation assay, as described above, is utilized to determine viability. The toxic dose is considered to be that where the mean counts are decreased by 20% relative the interested control. The next lower concentration is then used for the subsequent experiments. The degree of incorporation of the compound of interest can then be undertaken using the appropriate techniques. For example, PCR detection methods may be used for nucleic acid detection, and antibody binding assays may be used for proteins. Where the compound is being used for its cytotoxic capacity, thymidine incorporation may also be used to assess the effectiveness of delivery. Likewise, where the therapy increases viability relative to cells exposed to the compound but not provided with impulse transients, thymidine incorporation may also be used to gauge effectiveness when combined with the appropriate controls.

The general protocol for determining synergistic effects with test compound and high-pressure impulse transients involves the following steps:

1. Determine the toxicity of the experimental drug of interest as described above.
2. Incubate cells with the experimental drug overnight at the highest tested non-toxic concentration.
3. Wash the cells three times with RPMI and then put the cells on ice until needed.
4. Make the gel solution with and without the experimental drug.
5. Make the capillary tubes with the cells in the gel as described above. Typically, 40 tubes will be necessary to perform all the groups listed in the table below in 5 replicates.
6. Expose cell in gels to impulses.
7. Assay cells for thymidine and compound incorporation.

EXAMPLE 2

General Testing of Impulse Transient Therapy

In a particular example, EMT-6 cells were used to test the effects of the compound Photofrin II. Five repetitions were done for each combination tested, giving a total of 40 tubes tested; approximately 100,000 cells were present in each tube. An argon fluoride excimer laser (described above) was used to irradiate the polyamide, and the energy parameters were as follows: 400 mJ/centimeter$^2$ were used to strike a polyamide target which delivers approximately 400-bar impulse transients. A total 10 pulses were administered to each tube.

Cells were incubated with and without 1 µg/ml of Photofrin II overnight, followed by the dilution of cells to yield cell suspension of tumor cells. Cells were then placed in a liquid gel with and without 1 µg/ml of photofrin II. This was followed by exposure of cells to impulses. Following administration of impulses as indicated above, cells are incubated with tritiated thymidine. Thymidine incorporation is measured by recording counts using a scintillation counter. The results are summarized below.

| # | Incubate Cells with Photofrin | Photofrin II in Gel | Pressure Transients | Mean Counts | SD |
|---|---|---|---|---|---|
| 1 | + | + | + | 40,923 | 22,055 |
| 2 | + | + | − | 103,748 | 21,297 |
| 3 | + | − | + | 130,326 | 23,569 |
| 4 | + | − | − | 115,560 | 24,864 |
| 5 | − | + | + | 72,620 | 24,189 |
| 6 | − | + | − | 72,070 | 20,182 |
| 7 | − | − | + | 79,976 | 33,320 |
| 8 | − | − | − | 60,281 | 13,518 |

Summary of Compound Testing

These screening assays show that impulse transients can enhance the delivery of compounds to a variety of compounds when these compounds are administered at non-toxic levels to cells. As is clear from the data, a variety compounds show impulse transient-enhanced delivery. The most effective regimen occurs when the compound is both inside the cell and in the surrounding media at the time of exposure to the impulses.

EXAMPLE 3

Effects of Rise Time on Cell Viability

As described in detail above, a significant factor for enhancing the delivery of compounds to cells is the rise time of the impulse transients. In order to test the effects of the rise time, the tumor cell line EMT-6 and peripheral blood mononuclear cells (PBMC) were exposed to stress transients in vitro generated following ablation of polyamide transducers (as described above). Optical pulses having different durations were generated using separate argon-fluoride and krypton fluoride excimer lasers. The cells were then assayed for thymidine incorporation (as described above) as a test of viability. The results of these experiments are summarized in the following chart:

| Wavelength | 193 nm | | 248 nm | |
| Rise Time | <10 ns | | ~20 ns | |
| Cell Type | Fluence (mJ/cm$^2$) | Viability (% of control) | Fluence (mJ/cm$^2$) | Viability (% of control) |
| --- | --- | --- | --- | --- |
| EMT-6 | 560 | 48 | 580 | 123 |
| | 275 | 88 | 400 | 204 |
| PBMC | 550 | 34 | 570 | 77 |
| | 300 | 48 | 290 | 158 |

As is clear from the data, the impulse transients produced by these wavelengths have equal amplitudes for equal radiant exposures, but different rise times. Impulse transients produced by argon fluoride laser (193 nm) ablation of polyamide killed cells at both low and high fluences. On the other hand, cells exposed to impulse transients generated by krypton fluoride laser (248 nm) ablation of polyamide were stimulated to grow faster but the increased proliferation was overwhelmed at higher energies.

In a related experiment, mouse breast sarcoma cells (EMT-6) prepared as described above were exposed to impulse transients. Impulse transients were generated by ablation of the polyamide film and launched into the cell-containing medium. The argon fluoride and krypton fluoride ion excimer lasers described above were used to generate the two separate optical wavelengths (193 nm for the argon krypton laser; 248 for the krypton fluoride laser). Impulse transients were measured at the target site using a calibrated PVDF transducer, and were displayed using a digital storage oscilloscope (Tektronix 7934).

Figure 5:
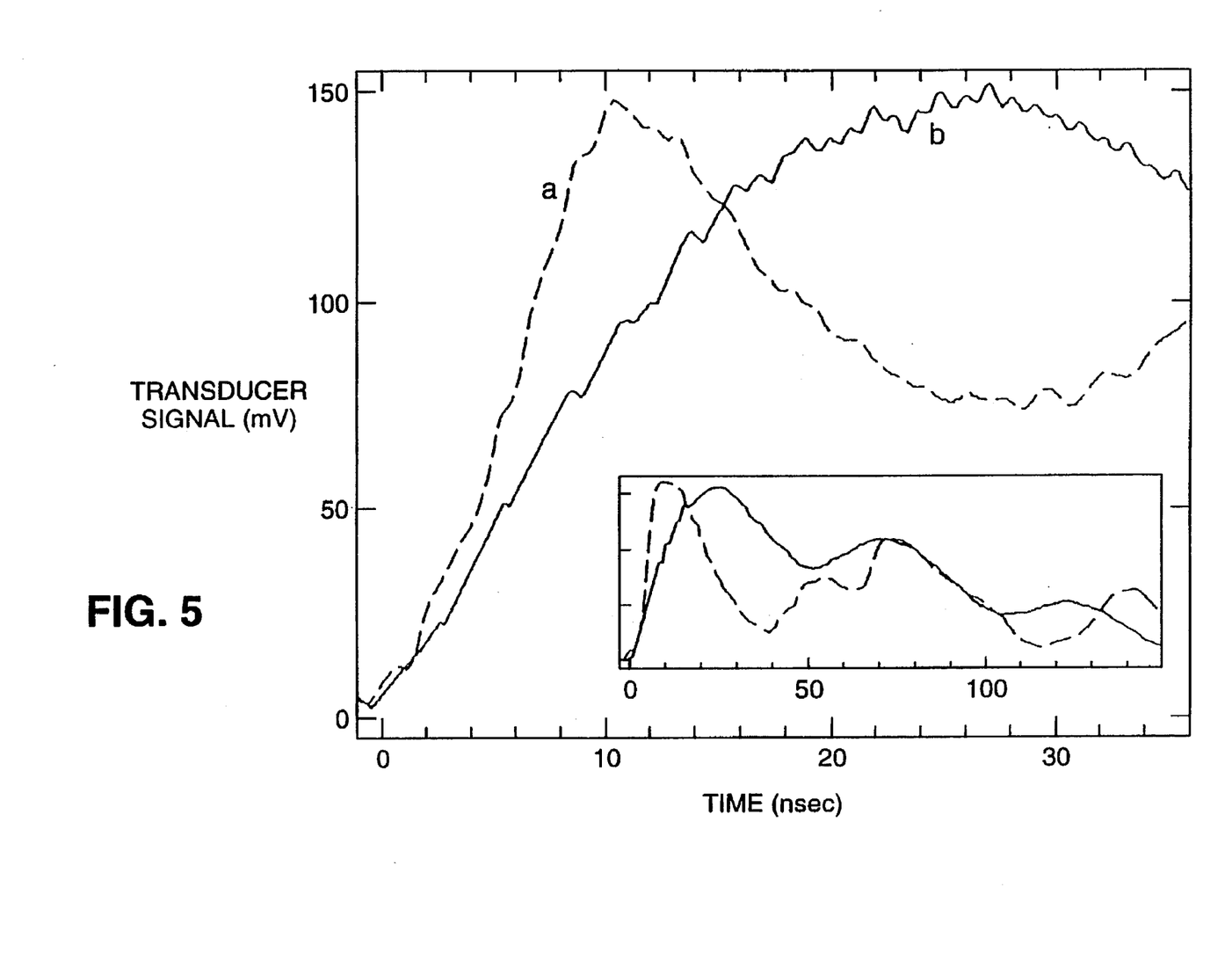
FIG. 5 is a plot showing the time dependencies of stress waves generated using argon fluoride (a) and krypton fluoride (b) lasers to ablate a polyamide transducer.
Figure 6A:
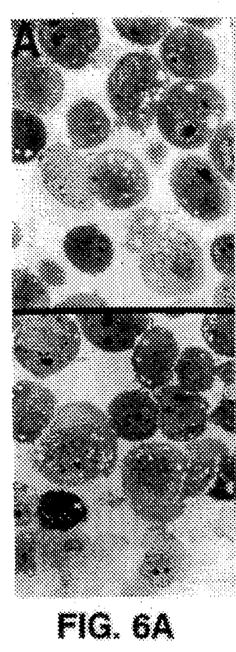
FIGS. 6A and 6C are electron micrographs of control groups of cells exposed to impulse transients generated by ablating polyamide transducers with light from, respectively, argon fluoride and krypton fluoride lasers.
Figure 6B:
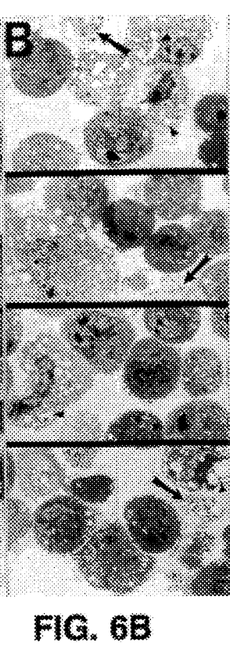
FIGS. 6B and 6D are electron micrographs of sample groups of cells exposed to impulse transients generated by ablating polyamide transducers with light from, respectively, argon fluoride and krypton fluoride lasers.
Figure 6C:
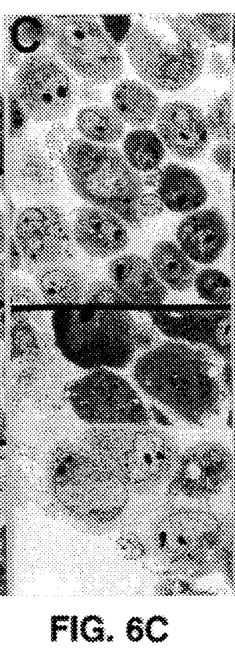
Figure 6D:
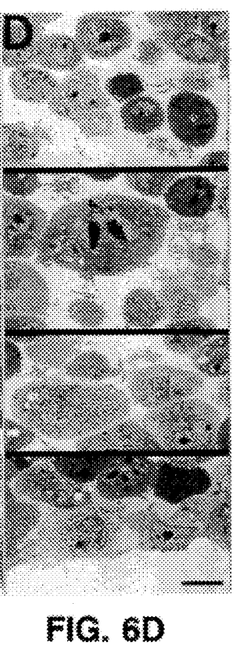

Impulse transients generated with the two different lasers exhibited different temporal properties. The argon fluoride laser ablates the polyamide film to generate an impulse transient with a rise time of between 7 and 12 nanoseconds and a pressure of about 410 barr, while the krypton fluoride laser induces a impulse transient with a rise time of between 22 and 20 nanoseconds and a pressure of about 390 bar. Both impulse transients have a duration of about 40–50 nanoseconds. The time-dependent properties of the impulse transients generated with the argon fluoride (a) and krypton fluoride (b) lasers are shown in FIG. 5.

After irradiation of sample and control groups, the cells were processed as described above, dehydrated in a graded ethanol series, and finally flat-embedded with Epon 812 (Electron Microscopy Sciences, Fort Washington, Pa.). One-micron-thick cross sections were cut through the samples for light microscopy. Thin sections were then stained with uranyl acetate and lead citrate, and then examined using a transmission electron microscope (CM-10, Philips, Eindehoven, The Netherlands).

Referring now to FIGS. 6A–6D, comparison of control cells (FIG. 6A) and sample cells (FIG. 6B) exposed to impulse transients generated by the argon fluoride laser indicate disruption of the cell wall and dilation of the endoplasmic reticulum as a result of the impulse transient. Control (FIG. 6C) and sample (FIG. 6D) cells exposed to impulse transients generated using the krypton fluoride laser show exhibit indistinguishable differences in viability, and also show only small differences when compared to the control cells of FIG. 6A. This indicates that the generated by the longer pulse width is ineffective in causing cellular disruption.

Figure 7:
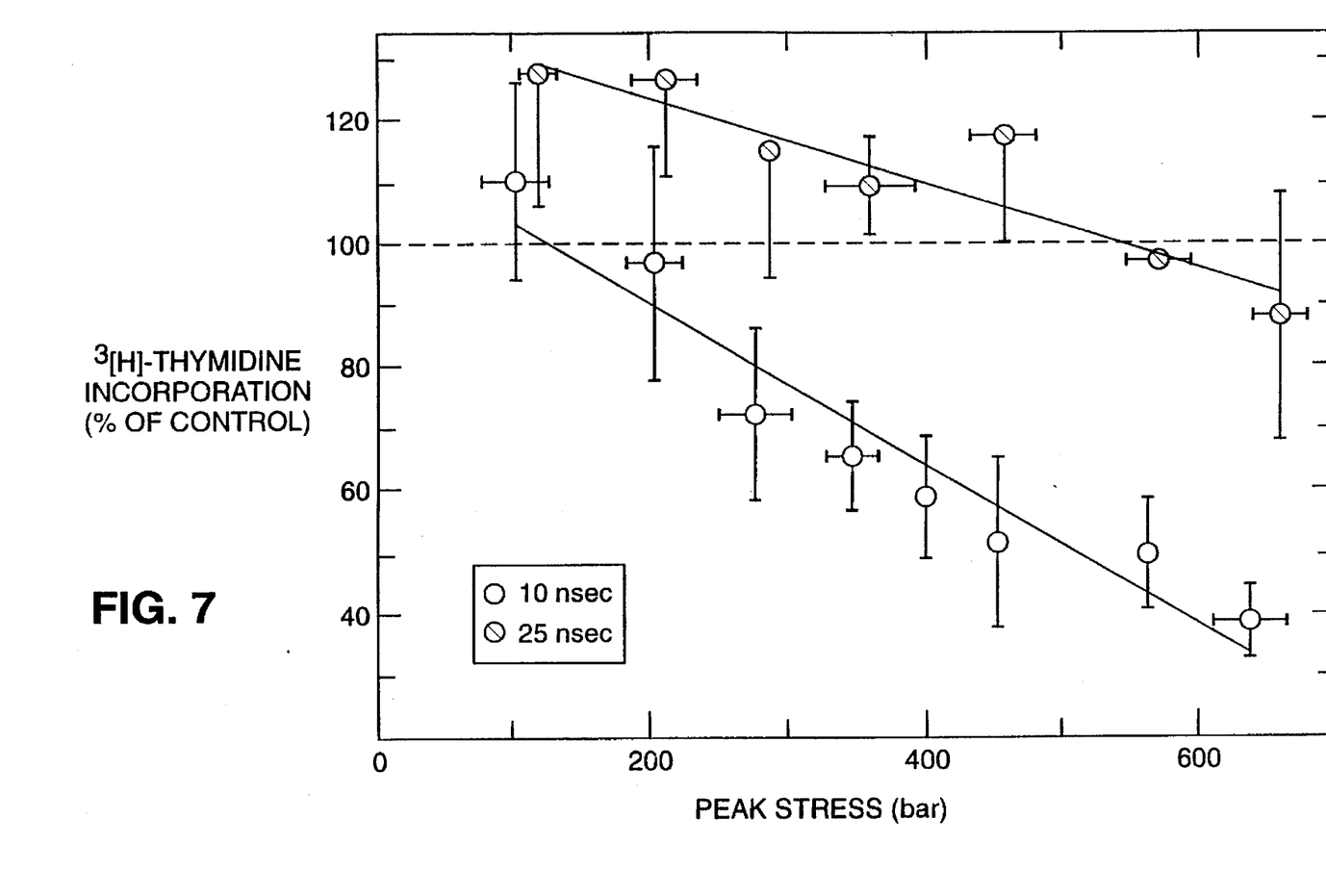
FIG. 7 is a plot showing cellular uptake of thymidine as a function of pressure for cells exposed to impulse transients having 10 and 25-nanosecond rise times; and, FIG. 8 is a plot showing cellular uptake of thymidine as a function of the rate of pressure increase for cells exposed to impulse transients having 10 and 25-nanosecond rise times.

Referring now to FIG. 7, tritiated thymidine is incorporated by samples cells exposed to 5 impulse transients having different peak pressures. In the figure, thymidine incorporation is measured by recording counts using a scintillation counter, and is given as a percent of thymidine incorporation of the control group. In general, this allows a measurement of cell proliferation. The salient feature in the plot is the difference in the response of cells exposed to impulse transients having different rise times. For example, at ~650-bar peak pressures, thymidine incorporation in cells exposed to impulse transients having 10-nanosecond rise times is roughly half (or less than half) of that corresponding to cells exposed to impulse transients having 25-nanosecond rise times. As is evident from the plot, at all pressures, thymidine incorporation was increased for cells exposed to the 10-nanosecond impulse transients.

Figure 8:
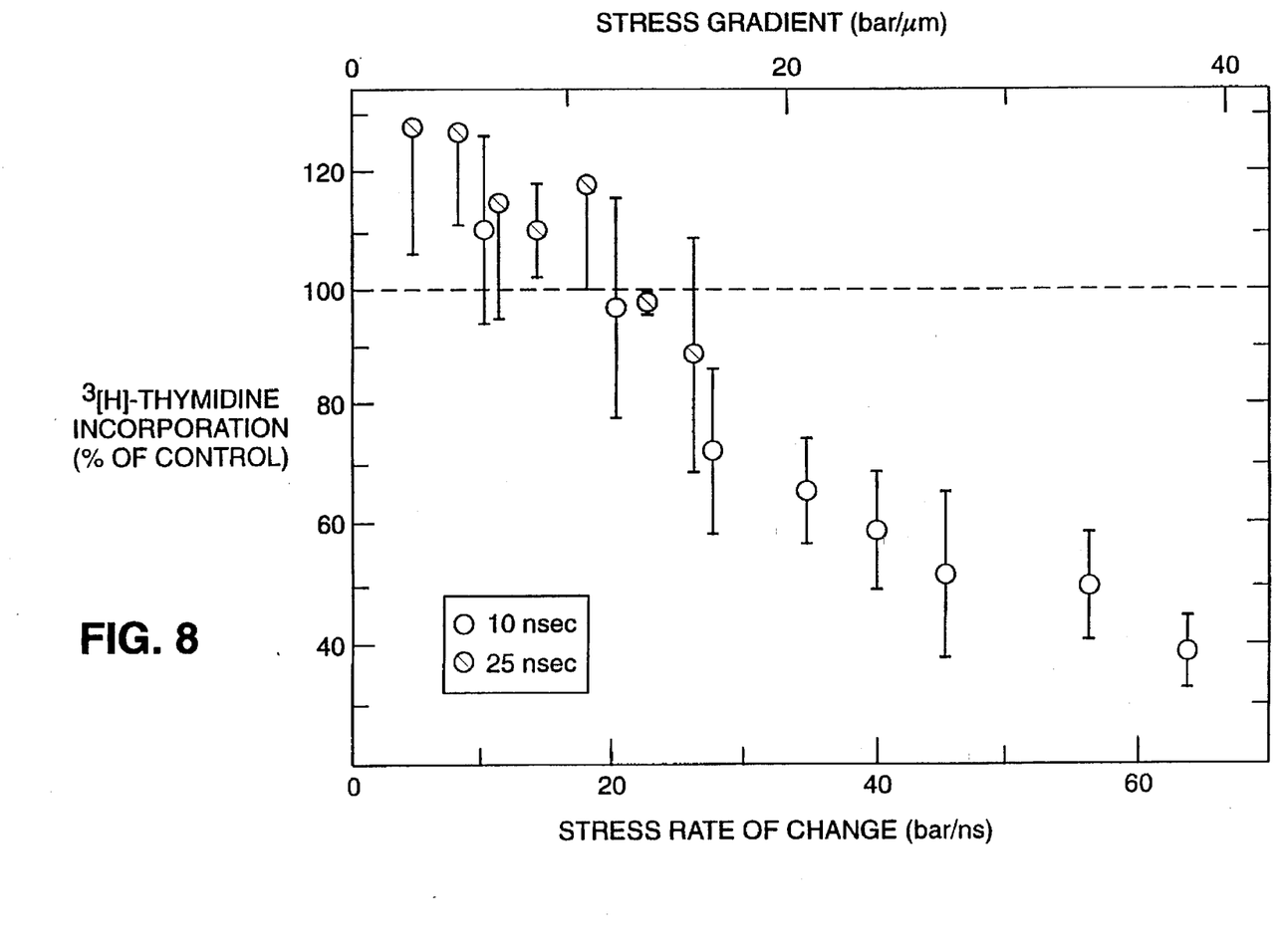

Referring now to FIG. 8, incorporation of tritiated thymidine is a function of the rate of pressure change in the exposed cells. The data show that the responses of cells to impulse transients follow the same trend as illustrated by FIG. 7. Here, the characteristics of the impulse transients, and particularly the rise times, significantly modify the response of cells; impulse transients having faster pressure rates of change result in a greater thymidine uptake by the cells.

EXAMPLE 4

Experiments Showing Impulse Enhanced Drug Uptake
Sample Experiment to Determine Impulse Enhanced Drug Uptake EMT-6 cells were used to test the effects of the compound Photofrin II. Five repetitions were done for each combination tested, giving a total of 40 tubes tested. The concentration of Photofrin II used was 1 µg/ml. Approximately 100,000 cells were present in each well. An argon fluoride excimer laser, described above, was used in the experiment to irradiate a polyamide target in contact with the cells. 16% of the full laser energy was used to irradiate a polyamide target which, in turn, delivers approximately 400-bar impulse transients to the cells. A total of 10 pulses were administered to each tube.

Cells were incubated with and without 1 µg/ml of Photofrin II overnight. Subsequent single cell suspension of tumor cells were made and cells were placed in liquid gel with and without 1 µg/ml of Photofrin II. Cells were then exposed to high-pressure impulses followed by lysis in 0.1M NaOH. Fluorescence was then measured using a fluorimeter. For each condition, there was at least a two fold increase in intracellular concentration of the drug following exposure to the impulses.

EXAMPLE 5

Applications of Impulse Transients to Gene Therapy

Impulse transients have been used in in vitro applications to introduce DNA to cells. Using a cell-supporting apparatus similar to that shown in FIG. 4, plasmids (approximately 700 kD) containing the gene for β-galactosidase were first exposed to the impulse transients in the absence of cells in order to monitor the effects of pressure on the nucleotide sequence. Following exposure to transients having magnitudes large enough to hemolyze red blood cells (i.e., roughly 2 kilobarrs), no change in mobility was observed in the DNA on agarose gel electrophoresis, indicating that there were no single-strand breaks in the DNA due to the impulse transient.

Once the benign nature of the impulse transients was established, COS cells were exposed to laser-induced impulse transients in the presence of the plasmids. Following exposure, the cells were returned to tissue culture for 24 hours. The cells were then assayed for the expression of β-galactosidase. While nearly 100% of the cells survived, 1 to 5% of the cells expressed the enzyme encoded by the plasmid DNA.

Other embodiments are within the scope of the following claims.

All references cited above are hereby incorporated by reference.

What is claimed is:

1. A method of increasing delivery of a compound from an exterior region to an interior region of a cell, said method comprising:

providing the compound in the exterior region proximal to a membrane of the cell, and exposing the membrane to a time-dependent impulse transient characterized by a rise time with a time constant of between 1 and 150 nanoseconds, and a magnitude of between 1 and 500 bars, wherein said exposing temporarily increases the permeability of the membrane to increase diffusion of the compound from the exterior region to the interior region, thereby enhancing the delivery of the compound to the cell.

2. The method of claim 1, wherein said exposing further includes generating the impulse transient in the exterior region of the cell, and then allowing the impulse transient to propagate until incident on the cell membrane.

3. The method of claim 2, wherein said generating comprises impulsively exciting the exterior region using a rapid, time-dependent force.

4. The method of claim 3, wherein the time-dependent force results from thermoelastic expansion of the exterior region.

5. The method of claim 4, wherein said generating comprises depositing over a short time period an amount of heat in the exterior region, said heat resulting in thermal expansion to cause the time-dependent force.

6. The method of claim 5, wherein the heat is generated using a pulsed optical source emitting a wavelength which is absorbed by a portion of the exterior region.

7. The method of claim 6, wherein the pulsed optical source is a laser.

8. The method of claim 3, wherein the rapid, time-dependent force is generated using a transducer.

9. The method of claim 8, wherein the transducer is in direct contact with the exterior region, and undergoes rapid displacement following application of an optical, thermal, or electric field to generate the impulse transient.

10. The method of claim 9, wherein the transducer is ablated using the applied optical field to cause the rapid displacement.

11. The method of claim 9, wherein the transducer undergoes piezoelectric expansion following application of the electrical field to cause the rapid displacement.

12. The method of claim 9, wherein the transducer undergoes thermal expansion following application of heat or a plasma to cause the rapid displacement.

13. The method of claim 1, wherein the time constant is below 35 nanoseconds.

14. The method of claim 1, wherein the pressure is between 250 and 350 bars.

15. The method of claim 1, wherein multiple impulse transients are used during said exposing step.

16. The method of claim 1, wherein said providing comprises directly applying the compound to the exterior region proximal to the cell.

17. The method of claim 16, wherein the compound is applied to a solution in the exterior region, and the cell is exposed to the impulse transient in vitro.

18. The method of claim 1, wherein said providing comprises administering the compound to a patient prior to said exposing, and the cells are exposed to the impulse transient in vivo.

19. The method of claim 18, wherein the patient is a human patient.

20. The method of claim 19, wherein the patient has a genetic disease.

21. The method of claim 1, wherein said exposing is extracorporeal.

22. The method of claim 1, wherein said exposing is during invasive surgery.

23. The method of claim 1, wherein the cell is a diseased cell comprised in a region of diseased tissue.

24. The method of claim 22, wherein the compound has a delivery index of at least 50, and the impulse transient is administered when a level of the compound in a region of healthy tissue is less than 50 percent of the level of said compound present in the diseased tissue.

25. The method of claim 1, wherein the compound comprises nucleic acid.

26. The method of claim 25, wherein said nucleic acid is DNA.

27. The method of claim 25, wherein the nucleic acid is RNA.

28. The method of claim 26, wherein the DNA comprises a gene.

29. The method of claim 1, wherein the cell is a member of a population of cells exposed to said time-dependent impulse transient.

30. The method of claim 28, wherein the compound is a non-cytotoxic compound, and a substantial fraction of the population remains viable following said exposing.

31. The method of claim 1, wherein more that one compound is delivered to the cell.

* * * * *